United States Patent
Marin et al.

(10) Patent No.: US 11,965,144 B2
(45) Date of Patent: Apr. 23, 2024

(54) PERFUME COMPLEX AND PERFUMED WATER COMPOSITION

(71) Applicant: EXPRESSIONS PARFUMÉES, Grasse (FR)

(72) Inventors: Christophe Marin, Nice (FR); Jennifer Buzzi, Grasse (FR)

(73) Assignee: EXPRESSIONS PARFUMÉES, Grasse (FR)

( * ) Notice: Subject to any disclaimer, the term of this patent is extended or adjusted under 35 U.S.C. 154(b) by 932 days.

(21) Appl. No.: 16/967,591

(22) PCT Filed: Feb. 7, 2019

(86) PCT No.: PCT/EP2019/052967
§ 371 (c)(1),
(2) Date: Aug. 5, 2020

(87) PCT Pub. No.: WO2019/154892
PCT Pub. Date: Aug. 15, 2019

(65) Prior Publication Data
US 2021/0230502 A1    Jul. 29, 2021

(30) Foreign Application Priority Data

Feb. 9, 2018 (FR) .................... 1851138
Sep. 10, 2018 (FR) .................... 1858100

(51) Int. Cl.
| | |
|---|---|
| C11B 9/00 | (2006.01) |
| A61K 8/34 | (2006.01) |
| A61K 8/39 | (2006.01) |
| C11D 1/72 | (2006.01) |
| C11D 3/20 | (2006.01) |
| C11D 3/50 | (2006.01) |
| C11D 17/00 | (2006.01) |
| A61Q 13/00 | (2006.01) |

(52) U.S. Cl.
CPC .......... *C11B 9/00* (2013.01); *A61K 8/345* (2013.01); *A61K 8/39* (2013.01); *C11D 1/72* (2013.01); *C11D 3/2048* (2013.01); *C11D 3/50* (2013.01); *C11D 17/0021* (2013.01); *A61K 2800/30* (2013.01); *A61K 2800/31* (2013.01); *A61Q 13/00* (2013.01)

(58) Field of Classification Search
CPC ...... A61K 8/39; A61K 8/345; A61K 2800/30; A61K 2800/31; C11B 9/00; C11D 3/2048; C11D 3/50; C11D 1/722; C11D 1/72; C11D 17/0021

USPC ........................................... 512/1
See application file for complete search history.

(56) References Cited

U.S. PATENT DOCUMENTS

| | | | |
|---|---|---|---|
| 6,110,449 A | 8/2000 | Bacon et al. | |
| 2013/0276808 A1* | 10/2013 | Molenda | A61K 8/84 |
| | | | 8/405 |
| 2013/0280175 A1 | 10/2013 | Banowski et al. | |
| 2014/0315772 A1 | 10/2014 | Cunningham | |

FOREIGN PATENT DOCUMENTS

| | | |
|---|---|---|
| DE | 102009060360 A1 | 6/2011 |
| EP | 1051148 A1 | 11/2000 |
| EP | 2471506 A1 | 7/2012 |
| WO | 2014187950 A1 | 11/2014 |

OTHER PUBLICATIONS

Rigano et al, Isopentyldiol for Improved Sensory, Formulation and Manufacturing benefits, Dec. 9, 2013, Cosmetics & Toiletries (Year: 2013).*
International Search Report issued in corresponding International Application No. PCT/EP2019/052967, dated Apr. 5, 2019, pp. 1-3, European Patent Office, Rijswijk, Netherlands.
Written Opinion issued in corresponding International Application No. PCT/EP2019/052967, dated Apr. 5, 2019, pp. 1-8, European Patent Office, Munich, Germany.

* cited by examiner

*Primary Examiner* — Jessica Whiteley
(74) *Attorney, Agent, or Firm* — HAUPTMAN HAM, LLP (57) ABSTRACT

The present invention relates to a perfume complex not comprising water and comprising three basic ingredients as follows: 15 to 45 wt. % perfume, 15 to 50 wt. % isopentyldiol and 15 to 30 wt. % C12-13 pareth-9, the percentages being expressed with respect to the total weight of the 3 basic ingredients. The invention also relates to a sprayable perfumed water composition in the form of microemulsion free from ethanol, with a high perfume dosage and transparent, said composition comprising 5 to 40 wt. % perfume, 5 to 30 wt. % C12-13 pareth-9, and 5 to 30 wt. % isopentyldiol, the percentages being expressed with respect to the total weight of said composition. The invention also relates to the cosmetic, detergent products and ambiance products comprising said composition.

24 Claims, 1 Drawing Sheet

PERFUME COMPLEX AND PERFUMED WATER COMPOSITION

The present application is a National Phase of International Application Number PCT/EP2019/052967, filed Feb. 7, 2019, which claims priority to French Application No. 1851138, filed Feb. 9, 2018, and French Application No. 1858100, filed Sep. 10, 2018.

FIELD OF THE INVENTION

The present invention relates to a perfume complex not comprising water and comprising three basic ingredients intended to form with an aqueous medium a composition and an advantageously sprayable perfumed water composition, comprising perfume, isopentyldiol and C12-13 pareth-9, advantageously in microemulsion form advantageously free from ethanol, advantageously at a high perfume dosage and advantageously transparent.

PRIOR ART

In the field of perfumery, a recurrent problem relates to the solubility of perfumes in water.

To ensure both sufficient solubility and olfactory performance for the user, it has proven necessary to add certain additives. Such additives particularly have the drawback of leaving a greasy and tacky texture and for the most part of irritating the skin. They also modify the properties of the solution containing same such as the viscosity and the proportion of foam formed.

Research studies have focused on the use of several solubilising agents and cosolvents, particularly vicinal diols, having low performances for high perfume dosages, such as 1,2-hexanediol. Such compounds have in some cases the drawback of being high-foam, high-tack, and must be heated in order to be used.

Numerous compositions currently on the market contain ethanol. However, ethanol is a VOC (Volatile Organic Compound), which is detrimental with respect to certain regulatory and environmental constraints. In parallel, research studies have helped demonstrate that the presence of water and the reduction or even absence of ethanol made it possible to increase the persistence of the perfume over time, prevent irritation and drying of the skin and hair, do away with risks associated with sun exposure and prevent any problem associated with storage, transport (customs), and flammability.

In order to remedy the drawbacks cited above, compositions based on cosolvents such as isosorbide, solketal, and ethers thereof, have been proposed, as in the document WO2014/187950 which uses in addition to one of these cosolvents Barsolve Plus, a mixture of 40-60% Trideceth-9, 20-40% PEG-40 Hydrogenated Castor oil, 5% Polysorbate-20, a solubilising agent marketed by Barnet. Compositions comprising ethoxylated oleyl alcohol (marketed under the name Ameroscol®) or sulphates, such as sodium lauryl sulphate and sodium laureth sulphate, by way of surfactants, have also been proposed. However, such compounds are irritant and drying for the skin and hair and are therefore to be avoided in the field of perfumery and cosmetics.

In perfumery, obtaining a scented mixture which is both versatile in terms of applications, stable, non-irritant for the skin and which has enhanced sensory properties, is the subject of ongoing research.

SUMMARY OF THE INVENTION

The invention relates to a perfume complex not comprising water and comprising three basic ingredients as follows: 15 to 45 wt. % perfume, 15 to 50 wt. % isopentyldiol and 15 to 30 wt. % C12-13 pareth-9, the percentages being expressed with respect to the total weight of the three basic ingredients.

The perfume complex according to the invention has the advantage of not containing water, which facilitates the transport thereof, the packaging thereof while being stable and non-irritant for the skin.

Advantageously, the perfume complex does not comprise ethanol.

The invention relates to the use of the perfume complex in an aqueous medium.

Indeed, the perfume complex is intended to be used in an aqueous medium to form particularly a composition according to the invention.

According to a further aspect, the invention relates to a composition comprising water and the perfume complex according to the invention.

According to an embodiment, the composition is free from ethanol.

According to an embodiment, the composition comprises from 30 to 40% perfume complex.

According to a further embodiment, the invention relates to a composition comprising 5 to 40 wt. % perfume, 5 to 30 wt. % C12-13 pareth-9, and 5 to 30 wt. % isopentyldiol, the percentages being expressed with respect to the total weight of said composition.

It also relates to a cosmetic base, detergent base or ambiance perfume comprising said composition, advantageously the composition is a cosmetic base, a detergent base, or an ambiance perfume.

It also relates to the use of said composition, said cosmetic base, said detergent base and said ambiance perfume to mask unpleasant odours.

DETAILED DESCRIPTION

The present invention thus relates to a perfume complex advantageously for obtaining a composition and an advantageously sprayable novel perfumed aqueous composition which are:
  (1) low-tack and low-foam,
  (2) compatible with any type of olfactory family,
  (3) of high perfume dosage,
  (4) which does not evaporate too quickly, and
  (5) which has sufficient solubility and olfactory performance.

Indeed, these five criteria may be contradictory. However, the present inventors were credited with discovering a perfume complex for obtaining a composition and an advantageously sprayable perfumed aqueous composition which offer an excellent compromise between these different criteria (1)-(5).

The perfume complex according to the invention ensures a balance between C12-13 pareth-9 and isopentyldiol. Indeed, the water-free formulation of the perfume complex with a view to the mixture thereof with water must meet complex stability constraints but also composition constraints mentioned above. The inventors established that:

a perfume complex containing less than 15 wt. % perfume will not be suitable for obtaining a sufficiently strong perfumed aqueous composition, a perfume complex containing more than 45 wt. % perfume will not be suitable for obtaining a transparent perfumed aqueous composition regardless of the olfactory family, a perfume complex comprising less than 15 wt. % C12-13 pareth-9 is not suitable for solubilising a perfume complex comprising 15 wt. % perfume and obtaining a transparent and strong perfumed aqueous composition, a perfume complex comprising more than 30 wt. % C12-13 pareth-9 induces an excessively tacky and foaming perfumed aqueous composition, a perfume complex comprising less than 15 wt. % isopentyldiol is not suitable for solubilising a perfume complex comprising 15 wt. % perfume and obtaining a transparent perfumed aqueous composition a perfume complex containing less than 15 wt. % isopentyldiol is not suitable for obtaining a perfumed aqueous composition with a low-tack texture.

a perfume complex comprising more than 50 wt. % isopentyldiol is not suitable for obtaining both a high perfume dosage and a C12-13 Pareth-9 dosage necessary for solubilisation with a view to a transparent aqueous composition.

Moreover, said composition developed by the present inventors is advantageous since it can be ethanol-free, transparent, stable, low-foam, non-irritant for the skin, pleasant once applied on the skin, has a viscosity similar to that of water, has good drying properties, has sufficient persistence and olfactory perception, and/or has enhanced sensory properties.

"Transparent" denotes that said composition is transparent for temperatures between 4° C. and 50° C. regardless of the perfume used. Transparent composition denotes a composition wherein the turbidity is less than 7 NTU (Nephelometric Turbidity Unit). The latter being preferentially measured using an HI88713 Iso Turbidimeter type turbidimeter of the make HANNA Instruments.

"Ethanol-free" denotes a composition containing 0 wt. % ethyl alcohol.

"Stable" denotes a composition which is not degraded over time and the compounds whereof will not react with one another. "Stable" denotes that the homogeneity, transparency, pleasant odour, and viscosity of the composition are retained. More particularly, the composition according to the present invention is stable under accelerated ageing after 24 h in UV (Suntest) and after 2 months at 25° C. and 45° C. compared with a sample remaining at 5° C., protected from light.

"Having a viscosity similar to that of water" denotes that the dynamic viscosity at 20° C. of said composition is between 1 and 50 mPa·s, preferentially between 1 and 40 mPa·s, and even more preferentially between 1 and 30 Pa·s. According to the present invention, the dynamic viscosity is measured with the Viscotester IQ viscosimeter, geometry CC27 DG/TI—01160025, at 20° C., at 500 $s^{-1}$ for 30 seconds.

"Good drying properties" denotes that it is possible to obtain a dry texture on spreading after a few minutes, preferentially after one minute, and even more preferentially after a few seconds.

"Compatible with any type of olfactory family" denotes that said composition can contain any type of perfume.

"High perfume dosage" denotes that the composition can contain up to 20%, up to 30% and up to 45 wt. % perfume.

The complex according to the invention does not comprise water and comprises the following three basic ingredients: 15 to 45 wt. % perfume, 15 to 50 wt. % isopentyldiol and 15 to 40%, preferentially 30 wt. % C12-13 pareth-9, the percentages being expressed with respect to the total weight of the 3 basic ingredients.

The complex is a concentrated composition form. The complex advantageously does not comprise ethanol. Preferentially, the complex consists of the three basic ingredients.

According to an embodiment, the complex comprises from 20 to 40 wt. % perfume, more preferentially from 27 to 31 wt. % perfume and by way of preferred example 28 wt. % perfume.

According to an embodiment, the complex comprises from 20 to 30 wt. % C12-13 pareth-9, more preferentially from 24 to 29 wt. % C12-13 pareth-9 and by way of preferred example 26 wt. % C12-13 pareth-9.

According to an embodiment, the complex comprises from 35 to 50 wt. % isopentyldiol, more preferentially from 42 to 47 wt. % isopentyldiol and by way of preferred example 46 wt. % isopentyldiol.

Advantageously, the complex according to the invention is not intended to be used as is but merely sold to facilitate transport and packaging. Preferentially, the complex is intended to be mixed with at least one aqueous solvent, preferably with at least water to form a composition according to the invention.

According to an embodiment, the composition comprises from 30 to 40% perfume complex, preferentially 35 wt. % of the total composition weight.

According to an embodiment, the composition according to the invention is a composition comprising 5 to 40 wt. % perfume, 5 to 30 wt. % C12-13 pareth-9, and 5 to 30 wt. % isopentyldiol, the percentages being expressed with respect to the total weight of said composition.

The composition according to the present invention is a perfumed composition.

"Perfumed composition" denotes a composition comprising a mixture of perfume substances, said perfume substances being in the isolated state, in solution or in suspension, in the usual diluents, solvents, or co-ingredients thereof. Such a composition is intended to provide a pleasant olfactory component.

"Perfume" or "perfume substance" denotes one or more natural or synthetic perfumed raw materials.

Such raw materials, whether they are natural or synthetic, can comprise esters, ethers, alcohols, aldehydes, ketones, lactones, acetals, nitriles, phenols, acids, terpenes, nitrogenous or sulphurated heterocyclic compounds, saturated or unsaturated, and complex products of natural origin.

Examples of esters comprise, but are not limited to, benzyl acetate, p-tert-butylcyclohexyl acetate, 3,7-dimethyl-1,6-octadien-3-yl acetate (linalyl acetate), dimethyl-benzyl-carbinyl acetate, phenylethyl acetate, 1,1-dimethyl-2-phenylethyl acetate, linalyl benzoate, ethyl-methyl-phenyl glycinate, allylcyclohexyl propionate, styrallyl propionate, benzyl salicylate, methyl-3-oxo-2-pentylcyclopentane acetate, prop-2-enyl-2,3-methylbutoxy acetate (allyl amyl glycolate, 2-propenyl ester of 3-methylbutoxy-acetic acid), phenylmethylic ester of acetic acid, isoamyl acetate (isopentyl acetate), cis-hex-3-enyl acetate ((Z)-hex-3-enyl acetate), citronellyl acetate (3,7-dimethyl-6-octen-1-ol acetate), hexyl acetate, isobornyl acetate (bicyclo[2.2.1] heptan-2-ol,1,7,7-trimethyl exo-acetate), methanyl acetate (alpha,alpha,4-trimethylcyclohexylmethyl acetate), ethyl acetate, prenyl acetate (3-methyl-2-butenyl acetate), triethyl citrate, 4-ter-Butylcyclohexyl acetate, (3R-(3alpha,3abeta, 6alpha,7beta,8aalpha))-Octahydro-3,6,8,8-tetramethyl-1H-3a-7-methanoazulene-5-yl acetate, 3,7-Dimethyl octa-1,6-diene-3-yl acetate, 1,4-Dioxacyclohexadecane-5,16-Dione, benzyl 2-hydroxybenzoate, (Z)-3-Hexenyl-2-hydroxybenzoate, 2-(1,1(Dimethylethyl) Cyclohexyl acetate, isopentyl acetate, Methyl Phenylacetate, (Z)-Hex-3-enyl acetate, 3,7-Dimethyl octa-1,6-diene-3-yl acetate, 3-Methyl-2-butenyl acetate, alpha-Methyl-Benzenemethanol acetate, methyl 2-aminobenzoate, 2-Propenyl-(cyclohexyloxy)acetate, methyl 2,4-dihydroxy-3,6-dimethylbenzoate, methyl 3-oxo-2-pentylcyclopentaneacetate, 3-alpha,4,5,6,7,7-alpha-Hexahydro-4,7-methano-1H-inden-6-yl propanoate, methyl 3-oxo-2-pentylcyclopentaneacetate, 2-(1,1-Dimethylethyl) Cyclohexyl acetate, hexyl-2-hydroxybenzoate (2-hydroxy-2-hexyl ester of benzoic acid), 3a,4,5,6,7,7a-Hexahydro-4,7-methanoinden-6-yl acetate, ethyl 2-methylbutyrate, 3a,4,5,6,7,7a-Hexahydro-4,7-methano-1H-inden-5-yl, 2-methylpropanoate, alpha,alpha-Dimethylphenethyl acetate, 3,7-Dimethyl octa-1,6-diene-3-yl acetate, exo-1,7, 7-trimethyl-bicyclo[2.2.1]heptan-2-ol acetate, ethyl hexanoate, 3,7-Dimethyl octa-1,6-diene-3-yl acetate, methyl 3-oxo-2-pentylcyclopentaneacetate, Methyl 2-(methylamino) benzoate, 10-Undecenoic acid, ethyl ester, methyl 2-methylpentanoate, cis-3,7-Dimethyl-2,6-octadienyl ethanoate, benzyl 2-hydroxybenzoate, (Z)-Hex-3-enyl acetate, 2-hydroxy-2-hexyl ester of benzoic acid, prop-2-enyl-2-cyclohexyloxyacetate (2-Propenyl-(cyclohexyloxy)acetate), Acetic acid, (3-Methylbutoxy), 2-Propenyl ester, 2-Phenylethanol, Hexyl acetate, (1R, 2S, 5R)-5-Methyl-2-(1-methylethyl)-cyclohexanol ethanoate, terpenyl acetate (4-methyl-1-propan-2-yl-1-cyclohex-2-enyl acetate), alpha-3,3-trimethylcyclohexyl-methyl formiate, 3-methylbutyl butanoate (iso amyl butyrate), alpha,alpha-dimethylphenethyl butanoate, 3-dihydrodicyclopentadien-2,3-yl acetate, prop-2-enyl, 3-cyclohexyl propanoate (allyl cyclohexane propionate), allyl heptanoate (2-propenyl heptanoate), 2-phenoxy-ethyl 2-methylpropanoate (phenoxy ethyl isobutyrate), ethyl 2-methyl-pentanoate, ethyl 2-methyl-butyrate (ethyl ester of 2-methyl-butanoic acid), 1,4-dioxacycloheptadecane-5,17-dione (Ethylene brassylate), (2S)-2-propyl-1, 1-dimethyl-propoxy propanoate ((2S)-propyl ester of 2-(1, 1-dimethylpropoxy)-propanoic acid), 2-tert-butylcyclohexyl acetate (2-(1,1-dimethylethyl)cyclohexyl acetate), ci-3-hexenyl salicylate, [(1S)-3-(4-methylpent-3-enyl)-1-cyclohex-3-enyl]methyl acetate, 3-pentyltetrahydro[2H]pyranyl acetate, linalyl propionate, cetyl acetate, cedryl acetate, anisyl acetate, nopyl acetate, neryl acetate, 3a,4,5,6,7,7a-hexahydro-4,7-methanoinden-6-yl acetate, 3a,4,5,6,7,7a-hexahydro-4,7-methano-1H-inden-6-yl propanoate, 2-propenyl 3-cyclohexanepropanoate, 1,2,3-triethyl 2-hydroxypropane-1,2,3-tricarboxylate, (2E)-3,7-dimethyl-octa-2,6-dien-1-yl acetate, 3,5,5-trimethylhexyl acetate, 3,7-dimethyl-octa-1,6-diene-3-yl acetate, cis-3,7-dimethyl-2,6-octadienyl ethanoate, 1-methylethyl ester of tetradecanoic acid, 3-methylbutylic ester of 2-hydroxy-benzoic acid, phenylmethylic ester of 2-hydroxy-benzoic acid, 2-hexyl ester of 2-hydroxy-benzoic acid, methyl ester of 2-hydroxy-Benzoic acid, ethyl ester of acetoacetic acid, 3,7-dimethyl-octa-1,6-diene-3-yl acetate, 1,2-diethyl ester of 1,2-benzenedicarboxylic acid, (Z)-hex-3-enyl 2-methylpropanoate, (4-methyl-1-propan-2-yl-1-cyclohex-2-enyl) acetate, 3a,4,5, 6,7,7a-hexahydro-4,7-methanoinden-6-yl acetate, ethyl 2,3-epoxy-3-phenylbutyrate, methyl 2-aminobenzoate, methyl 2-(methylamino)benzoate, methyl benzoate, methyl 2,4-dihydroxy-3,6-dimethylbenzoate, (3R-(3alpha,3beta,6beta, 7beta, 8alpha))-octahydro-6-methoxy-3,6,8,8-tetramethyl-1H-3a, 7-methanoazulene acetate, hexyl salicylate, 4-tert-butylcyclohexyl) acetate, methyl palmitate, 1,6-octadiene-3-ol, 3,7-dimethyl-acetate and triethyl citrate. Preferably, examples of esters comprise linalyl propionate, cetyl acetate, cedryl acetate, anisyl acetate, nopyl acetate, neryl acetate, (3R-(3alpha,3beta,6beta,7beta,8alpha))-octahydro-6-methoxy-3,6,8,8-tetramethyl-1H-3a,7-methanoazulene acetate, hexyl salicylate, 4-tert-butylcyclohexyl) acetate, methyl palmitate, 1,6-Octadien-3-ol, 3,7-dimethyl-acetate, linalyl acetate and triethyl citrate.

Examples of ethers comprise, but are not limited to, benzyl ether, ethyl ether, ambergris, diphenyl oxide, 4,6,6, 7,8,8-hexamethyl-1,3,4,6,7,8-hexahydrocyclopenta[g]isochromene, amber carane, 1,1-dimethoxy-2,2,5-trimethyl-4-hexene, 3,4,4a,5,8,8a-Hexahydro-3',7'-dimethylspiro(1,4-methanonaphthalene-2(1H),2'-oxirane), 2,4,6-Trimethyl-4-phenyl-1,3-dioxane, Benzene, 1,1'-Oxybis, Methyl 2-naphthyl ether, ethyl 2-naphthyl ether, 2,4-Dimethyl-4-phenyltetrahydrofuran, (ethoxymethoxy)cyclododecane, (E)-1-methoxy-4-(1-propenyl)-benzene, 1-methoxy-4-(2-propenyl)-benzene, Methyl cedryl ether and 2-naphthyl ethyl ether. Preferably, examples of ethers comprise, 1,1-dimethoxy-2,2,5-trimethyl-4-hexene, Methyl cedryl ether and 2-naphthyl ethyl ether.

Examples of alcohols comprise, but are not limited to, menthol ([1R-(1 alpha,2beta,5alpha)]-5-methyl-2-isopropylcyclohexanol), citronellol, geraniol, linalol (for example ethyl linalol and tetrahydro linalol), phenylethyl alcohol, terpineol, 2,6-dimethylheptan-2-ol, 2-methyl-1-phenylpropan-2-ol (dimethyl phenyl carbinol), 3-methyl-5-[2,2,3-trimethylcyclopent-3-en-1-yl]pent-4-en-2-ol, 2-phenylethanol, 2-ethyl-4-(2,2,3-trimethyl-1-cyclopent-3-enyl)but-2-en-1-ol, (E)-4-methyldec-3-en-5-ol, cinnamic alcohol (3-phenyl-2-propen-1-ol), 3,7-Dimethyl-6-octen-1-ol, p-menth-1-en-8-ol, cis-Hex-3-en-1-ol, 4-Methyl-3-decen-5-ol, 2,6-dimethyloct-7-en-2-ol, 1,1'-Oxydipropan-2-ol, 3,7-Dimethyl-1,6-nonadien-3-ol, 1,1'-Oxydipropan-2-ol, 2,6-dimethyloct-7-en-2-ol 3,7-Dimethyl octa-1,6-diene-3-ol, 2-ethyl-4-(2,2,3-trimethyl-3-cyclopenten-1-yl)-2-buten-1-ol, phenylmethanol, 4-Methyl-3-decen-5-ol, 2,6-Dimethyl-octan-2-ol, 3,7-Dimethyl-6-octen-1-ol, 4-(1,1-dimethylethyl)-Cyclohexanol, (2E)-3,7-dimethyl-2,6-Octadien-1-ol, Hexan-1-ol, exo-1,7,7-Trimethylbicyclo[2.2.1]heptan-2-ol, 2-(2,2,7,7-tetramethyltricyclo[6.2.1.0 (1,6)]undec-5(4)-en-5-yl)propan-1-ol, 1-Phenylethanol, 1,1'-Oxydipropan-2-ol, 3,7-Dimethyloctan-3-ol, cis-3,7-Dimethyl-2,6-octadien-1-ol, 3,7-Dimethyl-6-octen-1-ol, Hex-2-en-1-ol, 3,7-Dimethyl octa-1,6-diene-3-ol, 2-Methyl-4-phenylbutan-2-ol, 2,6-Octadien-1-ol, 3,7-dimethyl-, (2E)-, p-menth-1-en-8-ol, 3-Phenylpropan-1-ol, phenylmethanol, 2,6-dimethyloct-7-en-2-ol, alpha,beta,2,2,3-pentamethylcyclopent-3-ene-1-butanol, 3-(5,5,6-trimethylbicyclo[2.2.1]hept-2-yl) cyclohexan-1-ol (IBCH), cis-3-hexen-1-ol, methyl-trimethylbicyclo-hexylmethyl-cyclopropyl methanol benzyl alcohol, endo-1,7,7-trimethyl-bicyclo-[2.2.1]heptan-2-ol, 3,7-dimethyl-6-octen-1-ol, 3,7-dimethyl-1-octanol, (2E)-3,7-dimethyl-2,6-octadien-1-ol, cis-3,7-dimethyl-2,6-octadien-1-ol, 3,7-dimethyl-octa-1,6-diene-3-ol, 2-(4-methyl-1-cyclohex-3-enyl)propan-2-ol, 4-methyl-1-(1-methylethyl)-3-cyclohexen-1-ol, (1R, 2S, 5R)-5-methyl-2-(1-methylethyl)-cyclohexanol, (2E)-3,7-dimethyl-2,6-octadien-1-ol and 3-methylbutan-1-ol. Preferably, examples of alcohols comprise alpha,beta,2,2,3-pentamethylcyclopent-3-ene-1-butanol, 3-(5,5,6-trimethylbicyclo[2.2.1]hept-2-yl) cyclohexan-1-ol (IBCH), cis-3-hexenol, methyl-trimethylbicyclohexylmethyl-cyclopropyl methanol, 3-methylbutan-1-ol, ethyl linalol, tetrahydro linalol and [1R-(1alpha,2beta,5alpha)]-5-methyl-2-isopropylcyclohexanol (menthol).

Examples of aldehydes comprise, but are not limited to, linear alkanals comprising between 8 and 18 carbon atoms, 3,7-Dimethyl-2,6-octadienal (citral), citronellal, Cyclamen aldehyde, hydroxycitronellal, 3,7-Dimethyl-2,6-octadienal, Undecanal, alpha-methyl-4-(1-methylethyl)-Benzenepropanal, 3-(4-isopropylphenyl)-2-methylpropanal, 2,4-dimethylcyclohex-3-ene-1-carbaldehyde, 2,4-dimethylcyclohex-3-ene-1-carbaldehyde, (2E)-2-Dodecenal, Octanal, Lauryl aldehyde, Nonanal, (E)-2-Benzylideneoctanal, 2,4-dimethylcyclohex-3-ene-1-carbaldehyde, 3-(4-ethylphenyl)-2,2-dimethylpropanal, 4-Hydroxy-3-methoxybenzaldehyde, 3-(4-tert-butylphenyl)-2-methylpropanal, 3-(4-tert-butylphenyl)propanal, 2,6,10-trimethylundec-9-enal, 4(octahydro-4,7-methano[5H]inden-5-ylidene)butanal, 3-(3-propan-2-ylphenyl)butanal, 7-hydroxy-3,7-dimethyloctanal (hydroxycitronellal, 3,7-dimethyl-7-hydroxy-octane-1-al), 4-(4-hydroxy-4-methylpentyl)cyclohex-3-ene-1-carbaldehyde, octahydro-5-methoxy-4,7-methano-1H-indene-2-carboxaldehyde, alpha-methyl cinnamic aldehyde (2-methyl-3-phenyl-2-propenal), 4-methoxybenzaldehyde (Anisic aldehyde), C10 aldehyde (decanal), undec-10-enal, C12 aldehyde (lauric or dodecanal), methyl-nonyl acetaldehyde (2-methylundecanal), C16 aldehyde, C6 aldehyde (hexanal), cinnamic aldehyde (3-phenyl-2-propenal), 3-ethyoxy-4-hydroxybenzaldehyde (Ethylvanillin), hexyl cinnamic aldehyde (2-benzylideneheptanal), 3-phenylbutanal (3-phenylbutyraldehyde), 2,4-dimethylcyclohex-3-ene-1-carbaldehyde, 5-heptanal, 2,6-dimethylhept-5-enal, 4-hydroxy-3-methoxybenzaldehyde (Vanillin), alpha-methyl-1,3-benzodioxole-5-propionaldehyde, 4-isopropylbenzaldehyde, 3,7-dimethyl-6-octenal, 3,7-dimethyl-2,6-octadienal, 4-(4-hydroxy-4-methylpentyl)-3-cyclohexene-1-carboxaldehyde, trans-hex-2-enal, 2,4,6-trimethyl-3-cyclohexene-1-carboxaldehyde, 2-(4-tert-butylbenzyl) propionaldehyde and benzaldehyde. Preferably, examples of aldehydes comprise 2,4-dimethylcyclohex-3-ene-1-carbaldehyde, 5-heptanal, 2,6-dimethyl-hept-5-enal, 4-hydroxy-3-methoxybenzaldehyde (Vanillin), alpha-methyl-1,3-benzodioxole-5-propionaldehyde, citral and benzaldehyde.

Examples of ketones comprise, but are not limited to, ionones, isomethylionone, methyl cedryl, (E)-1-(2,6,6-trimethyl-1-cyclohex-2-enyl)but-2-en-1-one (alpha-damascone), 3-methyl-2-[(2Z)-pent-2-en-1-yl]cyclopent-2-en-1-one (cis-jasmone), 4-(4-methoxyphenyl)-butan-2-one, 4(3)-(4-methylpent-3-enyl)cyclohex-3-enecarbaldehyde, 1-(1,2,3,4,5,6,7,8-octahydro-2,3,8,8-tetramethyl-2-naphthalenyl) ethanone, 3-Methyl-4-(2,6,6-trimethyl-2-cyclohexenyl)-3-buten-2-one, (E)-4-(2,6,6-trimethyl-1-cyclohexen-1-yl)-3-buten-2-one, E)-4-(2,6,6-trimethylcyclohex-2-eneyl)-but-3-en-2-one, 7-Methyl-2H-benzo-1,5-dioxepin-3(4H)-one, 1-(2,6,6-Trimethyl-1,3-cyclohexadienyl)-2-buten-1-one, Methyl hydroxypyrone, 2,2,5-Trimethyl-5-pentylcyclopentan-1-one, 1-(5,5-Dimethyl-1-cyclohexenyl)pent-4-en-1-one, 3-Methyl-4-(2,6,6-trimethyl-2-cyclohexenyl)-3-buten-2-one, 2-[2-(4-Methyl-3-cyclohexen-1-yl)propyl]-cyclopentanone, 1-(1,2,3,4,5,6,7,8-octahydro-2,3,8,8-tetramethyl-2-naphthalenyl)ethanone, (E)-4-(2,6,6-trimethyl-1-cyclohexen-1-yl)-3-buten-2-one, 4-Phenylbutan-2-one
2-Cyclohexyl-1,6-heptadien-3-one, 1-(5,5-Dimethyl-1-cyclohexenyl)pent-4-en-1-one, 2-Buten-1-one, 1-(2,6,6-trimethyl-3-cyclohexen-1-yl)-, 2H-1-Benzopyran-2-one, 1-spiro(4.5)-7-decen-7-yl-4-penten-1-one and 1-spiro(4.5)-6-decen-7-yl-4-penten-1-one, (E)1-(2,6,6-Trimethyl-2-cyclohexen-1-yl)-2-buten-1-one, (E)-4-(2,6,6-trimethyl-1-cyclohexen-1-yl)-3-buten-2-one, Dihydro-5-pentyl-2(3H)-furanone, 2,2,5-Trimethyl-5-pentylcyclopentan-1-one, 1-(1,2,3,4,5,6,7,8-octahydro-2,3,8,8-tetramethyl-2-naphthalenyl) ethanone, methyl cedryl ketone, 7-methylbenzo[b][1,4] dioxepin-3-one, 1,7,7-trimethylbicyclo[2,2,1]heptan-2-one, 1-benzopyrane-2-one (Coumarin), 1-(2,6,6-trimethyl-1-cyclohex-3-enyl)but-2-en-1-one, butan-2,3-dione (Diacetyl), 1-(1,2,3,4,5,6,7,8-octahydro-2,3,8,8,-tetramethyl-2-naphthyl)ethan-1-one, irones, 1-(2-naphthalenyl)ethanone (2-acetonaphthone), menthone, carvone, 3-methyl-2-pentyl-2-cyclopentenone, 1-(2,6,6-trimethyl-3-cyclohexen-1-yl)-2-buten-1-one, 1-(2,6,6-trimethyl-2-cyclohexenyl)hepta-1,6-dien-3-one, 2-ethyl-3-hydroxy-4H-pyran-4-one, (5R)-2-methyl-5-prop-1-en-2-ylcyclohex-2-en-1-one, 1-(6-tert-butyl-1,1-dimethyl-2,3-dihydro-1H-inden-4-yl)ethanone, 1-(5,6,7,8-tetrahydro-3,5,5,6,8,8-hexamethyl-2-naphthyl) ethan-1-one, 4-(2,6,6-trimethylcyclohex-2-enyl)-but-3-ene-2-one, octan-2-one, 1-(1,2,3,4,5,6,7,8-Octahydro-2,3,8,8-Tetramethyl-2-Naphthyl)Ethan-1-one and 1,3,4,6,7,8a-Hexahydro-1,1,5,5-tetramethyl-2H-2,4a-methanonaphthalen-8(5H)-one. Preferably, examples of ketones comprise irones, 1-(2-naphthalenyl)ethanone (2-acetonaphthone), menthone, carvone, 3-methyl-2-pentyl-2-cyclopentenone, 1-(1,2,3,4,5,6,7,8-Octahydro-2,3,8,8-Tetramethyl-2-Naphthyl)Ethan-1-one and 1,3,4,6,7,8a-Hexahydro-1,1,5,5-tetramethyl-2H-2,4a-methanonaphthalen-8(5H)-one.

Examples of lactones comprise, but are not limited to gamma decalactone (decan-4-olide), Decan-5-olide, Decan-4-olide, Undecan-4-olide gamma undecalactone (undecan-4-olide), cis-jasmone lactone, gamma undecalactone, delta octalacone, delta decalactone and hexahydro-3,6-dimethyl-2(3H)-benzofuranone. Preferably, examples of lactones comprise gamma undecalactone, delta octalacone, delta decalactone and hexahydro-3,6-dimethyl-2(3H)-benzofuranone.

Examples of acetals comprise, but are not limited to, 2,4-dimethyl tetrahydroindenodioxin, phenylacetic aldehyde diacetal, phenylacetaldehyde glycerylacetal, citral diethyl acetal, citral dimethyl acetal, 2,6-octadienal, 1,1-dimethoxy-2-phenylethane and isomerised 3,7-dimethyl acid. Preferably, examples of acetals comprise phenylacetaldehyde glycerylacetal, citral diethyl acetal, citral dimethyl acetal, 2,6-octadienal and isomerised 3,7-dimethyl acid.

Examples of nitriles comprise, but are not limited to, 3,7-dimethyloct-6-ene nitrile (citronellyl nitrile), tridec-2-enenitrile, 3-phenyl-2-propenenitrile, 3,7-Dimethyl-6-enenitrile, dodecanenitrile and 3,7-dimethylnona-2,6-dienenitrile. Preferably, examples of nitriles comprise tridec-2-enenitrile, 3-phenyl-2-propenenitrile, dodecanenitrile and 3,7-dimethylnona-2,6-dienenitrile.

Examples of phenols comprise, but are not limited to, eugenol (2-methoxy-4-(2-propenyl)-phenol), iso-eugenol, 5-methyl-2-(1-methylethyl)-phenol, 2-ethoxy-4-methylphenol, 2-isopropyl-5-methylphenol, 5-methyl-2-(1-methylethyl)-Phenol, 2,6-di-tert-butyl-p-cresol and 2-ethoxy-4-(methoxymethyl)-phenol.

Examples of acids comprise, but are not limited to, pentanoic acid, butyric acid and 2-methylpent-2-en-1-oic acid.

Examples of terpenes such as cyclic (for example sesquiterpenic) or non-cyclic terpenic hydrocarbons, comprise, but are not limited to, limonene, 1-methyl-4-isopropenyl-1-cyclohexene, 1-methyl-4-isopropyl-1,4-cyclohexadiene, 7-methyl-3-methyleneocta-1,6-diene, 1-methyl-4-(1-methylethyl)-1,3-cyclohexadiene, 2,6,6-trimethylbicyclo[3.1.1] hept-2-ene, 6,6-dimethyl-2-methylenebicyclo[3.1.1]heptane, 2,2-dimethyl-3-methylenebicyclo-[2.2.1]-heptane, (3R-(3alpha,3abeta,6beta,7beta,8aalpha))-Octahydro-6-methoxy-3,6,8,8-tetramethyl-1H-3a,7-methanoazulene, 4,11,11-trimethyl-8-methylene-(1R,4E,9S)-Bicyclo[7.2.0]undec-4-ene, [1R,(1R*,4E,9S*)]-4,11,11-trimethyl-8-methylene-bicyclo[7.2.0]undec-4-ene, 1-methyl-4-(1-methylethyl)benzene and sesquiterpene essential oils. Preferably, examples of terpenes comprise sesquiterpene essential oils.

Examples of saturated or unsaturated, nitrogenous or sulphurated heterocyclic compounds comprise, but are not limited to indole, 1,3-benzopyrrole, tetrahydro-4-methyl-2-(2-methyl-1-propenyl)-2H-pyrane, 2-methyl-pyrazine, 4-methyl-5-hydroxyethyl thiazole (2-(4-methylthiazol-5-yl) ethanol), 6-tert-butylquinoline, 6-(isopropyl)quinoline, (3aR-(3aalpha,5abeta,9aalpha,9bbeta))-Dodecahydro-3a,6,6,9a-tetramethylnaphtho(2,1-b)furan, 2-Isopropyl-4-methyl-1,3-thiazole, cis-2-methyl-4-propyl-1,3-oxathiane, 6(8)-(1-Methylpropyl)Quinoline and pyrazines. Preferably, examples of saturated or unsaturated, nitrogenous, or sulphurated heterocyclic compounds comprise 6-tert-butylquinoline, 6-(isopropyl)quinoline, cis-2-methyl-4-propyl-1,3-oxathiane, 6(8)-(1-Methylpropyl)Quinoline and pyrazines.

Examples of complex products of natural origin comprise, but are not limited to, essential oils extracted from the different plant parts (flowers, stems, leaves, fruit, peels, roots, woody parts, herbs, needles, sap, and gums), resinoids, concretes, or absolutes obtained therefrom. Preferably, examples of complex products of natural origin comprise white wormwood oil (*Artemisia herba-alba*), *Pogostemon Cablin* Leaf Oil, *Citrus nobilis* peel oil, *Barosma betulina* leaf oil (*Barosma betulina* Leaf Extract), *Citrus limon* Peel extract, *Eucalyptus globulus* leaf oil, *Dipterocarpus turbinatus* oil (*Dipterocarpus turbinatus* Balsam Oil), *Pogostemon cablin* leaf oil, *Rosmarinus officinalis* leaf oil, *Juniperus virginiana* oil, field mint leaf oil (*Mentha Arvensis*), spearmint leaf oil (*Mentha viridis*), *Citrus aurantium dulcis* peel oil, *Citrus aurantium dulcis* peel extract, Mediterranean cypress leaf oil (*Cupressus sempervirens*), patchouli leaf oil (*Pogostemon cablin*), Texas cedarwood oil (*Juniperus mexicana*) and Lavandin oil (*Lavandula hybrida*).

The perfume according to the invention can comprise ingredients of natural or synthetic origin. The choice of this perfume is dependent, on one hand, on the scented effect sought and, on the other, on the nature of the product containing same.

According to a possibility, the perfume complex and the composition according to the invention comprises perfumes containing less than 18 wt. % branched alcohol with at least 8 carbon atoms with respect to the total weight of said perfume.

The perfume can be used in proportions varying according to the intended use.

The perfume can represent 5 to 40%, 7 to 30% or indeed 10 to 20 wt. % with respect to the total weight of said composition.

C12-13 pareth-9 is an advantageous non-ionic surfactant given the low cost thereof and the biodegradability thereof under aerobic conditions. Moreover, C12-13 pareth-9 is non-irritant for the skin and has no odour. In particular, the biodegradability of C12-13 pareth-9 is greater than 60% as per the OCBE 301B standard.

C12-13 pareth-9 can be used in proportions varying according to the intended use.

Preferably, C12-13 pareth-9 represents 5 to 30%, preferentially 7 to 25% or even more preferentially 9 to 20 wt. % with respect to the total weight of said composition.

Isopentyldiol (also known as isoprene glycol or 3-methyl 1,3-butanediol) is a hydrophilic co-solvent which makes it possible to reduce the quantity of surfactants to be added in order to obtain a stable composition. Furthermore, this co-solvent makes it possible to obtain translucid compositions, does not denature the perfumes, is neither tacky, nor irritant and is not sensitive to oxidation by air. It also makes it possible to obtain a dry texture on spreading after a few minutes, preferentially after one minute, and even more preferentially after a few seconds.

Isopentyldiol is not a vicinal diol.

"Vicinal diol" denotes an alcohol comprising at least two hydroxyl groups, two of the hydroxyl groups being attached to adjacent carbon atoms.

Isopentyldiol can be used in proportions varying according to the intended use.

Preferably, isopentyldiol represents 5 to 30%, preferentially 7 to 25% or even more preferentially 10 to 20 wt. % with respect to the total weight of said composition.

According to a specific embodiment, the composition according to the invention further comprises at least one additive chosen among anti-foaming agents, antioxidant agents, chelating agents, UV filters, preservatives, thickening agents, cosmetic active ingredients, hydrating agents, humectants, demulcents, pigments, colorants, cooling agent, pH-adjusting agents, bactericidal agents, bacteriostatic agents, insecticides, repellents and mixtures thereof.

The additives are present in a quantity ranging from 0 to 5%, preferably from 0.001 to 2%, preferentially 0.05 to 1%, and even more preferentially from 0.001 to 0.1 wt. % with respect to the total weight of said composition.

Preferably, the composition according to the present invention comprises:
  5.00% to 40.00%, preferentially 10.00% to 30.00%, even more preferentially 20.00 wt. % perfume with respect to the total weight of said composition,
  5.00% to 30.00%, preferentially 10.00% to 25.00%, even more preferentially 20.00 wt. % 012-13 Pareth-9 with respect to the total weight of said composition, and
  5.00% to 30.00%, preferentially 10.00% to 25.00%, even more preferentially 20.00 wt. % isopentyldiol with respect to the total weight of said composition, and Preferably, the composition according to the present invention comprises:
  5.00% to 40.00%, preferentially 6.00% to 30.00%, even more preferentially 7.00 wt. % perfume with respect to the total weight of said composition,
  5.00% to 30.00%, preferentially 7.00% to 20.00%, even more preferentially 8.00 wt. % C12-13 Pareth-9 with respect to the total weight of said composition, and
  5.00% to 30.00%, preferentially 6.00% to 20.00%, even more preferentially 7.00 wt. % isopentyldiol with respect to the total weight of said composition, and Preferably, the composition according to the present invention comprises:
  5.00% to 40.00%, preferentially 5.00% to 30.00%, even more preferentially 5.00 wt. % perfume with respect to the total weight of said composition,
  5.00% to 30.00%, preferentially 7.00% to 20.00%, even more preferentially 9.00 wt. % C12-13 Pareth-9 with respect to the total weight of said composition, and
  5.00% to 30.00%, preferentially 10.00% to 20.00%, even more preferentially 15.00 wt. % isopentyldiol with respect to the total weight of said composition, and Preferably, the composition according to the present invention comprises:

5.00% to 40.00%, preferentially 10.00% to 30.00%, even more preferentially 12.00 wt. % perfume with respect to the total weight of said composition, 5.00% to 30.00%, preferentially 10.00% to 20.00%, even more preferentially 13.00 wt. % C12-13 Pareth-9 with respect to the total weight of said composition, and 5.00% to 30.00%, preferentially 10.00% to 20.00%, even more preferentially 15.00 wt. % isopentyldiol with respect to the total weight of said composition.

Preferably, the composition according to the present invention comprises:

5.00% to 40.00%, preferentially 10.00% to 30.00%, even more preferentially 15.00 wt. % perfume with respect to the total weight of said composition, 5.00% to 30.00%, preferentially 10.00% to 20.00%, even more preferentially 15.00 wt. % C12-13 Pareth-9 with respect to the total weight of said composition, and 5.00% to 30.00%, preferentially 10.00% to 20.00%, even more preferentially 15.00 wt. % isopentyldiol with respect to the total weight of said composition.

Preferably, the composition according to the present invention comprises:

5.00% to 40.00%, preferentially 10.00% to 40.00%, even more preferentially 40.00 wt. % perfume with respect to the total weight of said composition, 5.00% to 30.00%, preferentially 15.00% to 25.00%, even more preferentially 25.00 wt. % C12-13 Pareth-9 with respect to the total weight of said composition, and 5.00% to 30.00%, preferentially 10.00% to 20.00%, even more preferentially 15.00 wt. % isopentyldiol with respect to the total weight of said composition.

Preferably, the composition according to the present invention comprises:

5.00% to 40.00%, preferentially 10.00% to 40.00%, even more preferentially 10.00 wt. % perfume with respect to the total weight of said composition, 5.00% to 30.00%, preferentially 15.00% to 25.00%, even more preferentially 16.00 wt. % isopentyldiol with respect to the total weight of said composition, and 5.00% to 30.00%, preferentially 10.00% to 20.00%, even more preferentially 9.00 wt. % C12-13 Pareth-9 with respect to the total weight of said composition.

All the percentages are given with respect to the total weight of said composition.

Preferably, the composition is an aqueous composition.

Preferably, the composition according to the invention is a microemulsion.

"Microemulsion" denotes an emulsion wherein the micelles have a size between 100 and 200 nm, and therefore invisible to the naked eye, thus giving a transparent appearance.

Preferably, the composition according to the invention is free from ethanol.

The composition according to the invention comprises a very low Volatile Organic Compound (VOC) content, particularly less than or equal to 400 g/L.

According to a specific embodiment, the composition is free from Volatile Organic Compounds (VOC).

Preferably, the composition according to the invention does not contain a co-solvent chosen in the group comprising isosorbide, solketal and ethers thereof.

Preferably, the composition according to the invention does not contain sulphates.

Preferably, the composition according to the invention does not contain vicinal diol.

The composition according to the invention is intended to be applied or sprayed onto a surface or in the air in order to confer a pleasant odour.

"Pleasant odour" denotes an odour which is detected by the human sense of smell and which is perceived as pleasant.

The present invention also relates to a cosmetic base comprising the composition according to the present invention.

"Cosmetic base" denotes a cosmetic product or a hygiene care product in the form of a cream, an emulsion, a foam, a wax, an oil, a lotion, a gel, a suspension, a mist, a solution, a powder, a balm, a serum, a mask, or an exfoliation treatment. Examples of cosmetic products, comprise, but are not limited to, perfumes, eaux de parfums, eaux de toilette for adults and babies, hair products, shaving and after-shave products, essential oils, skin care products, deodorants, antiperspirants, depilatory products, self-tanning products, sunscreens, makeup products, body mist, etc. Examples of hygiene care products comprise, but are not limited to, refreshing and/or cleansing wipes, talcs, nappies, bibs, handkerchiefs, paper towels, soaps, shower gels, shampoos and other body wash products, oral care products, feminine hygiene products, deodorisers, deodorants, etc.

The present invention also relates to a detergent base comprising the composition according to the present invention.

"Detergent base" denotes care or cleaning products. Examples of care or cleaning products comprise, but are not limited to, detergents for surfaces, for fabrics or for dishes, bleaching agents, softeners, washing machine or dryer perfumes, stripping products, varnishes, and other household products.

The present invention also relates to weedkilling and fertiliser products comprising the composition according to the present invention.

The present invention also relates to an ambiance perfume comprising the composition according to the present invention.

"Ambiance perfume" denotes products intended to perfume the air. Ambiance products can, non-restrictively, be contained in aerosols, vaporisers, sprays, candles, perfumed gels, solid substrates, perfume burners, stick diffusers, incense, beads, and perfume diffusers. The ambiance perfume according to the present invention can be used for public, professional, or private enclosed spaces; for example, the car, the home, administrative buildings, public transport, museums, historic monuments, churches, cellars, schools, restaurants, cinemas, hospitals, factories, water or waste treatment plants, shops, and hotels. The ambiance perfume can also be used in air conditioning systems.

The present invention also relates to materials comprising or coated with the composition according to the invention, particularly polymers such as for example plastics, macromolecules such as for example cellulose, etc. For example, the composition according to the invention may be used as a perfume for laundry particularly as pillow mist.

The composition according to the invention is intended to be applied in optionally concentrated form in cosmetic bases, detergent bases, or ambiance perfumes.

The present invention also relates to the use of the composition according to the invention for preparing a cosmetic composition, a detergent base, or an ambiance perfume.

The present invention also relates to the use of the composition according to the invention, the cosmetic base, the detergent base, or the ambiance perfume to mask unpleasant odours.

"Unpleasant odours" denotes odours which are detected by the human sense of smell and which are perceived as offensive or unpleasant. According to the present invention, the unpleasant odours to be masked can result intrinsically from the cosmetic, detergent base or ambiance perfume per se, or indeed originate from the external environment.

"Mask unpleasant odours" denotes the modification of the qualitative perception of the odour by adding a substance or a substance mixture capable of providing a new, distinct, and pleasant odour.

In a specific embodiment, the composition according to the present invention masks unpleasant odours without for all that degrading the molecules responsible for the unpleasant odours. Indeed, the molecules of the composition mask the smell of the molecules responsible for the unpleasant odours.

The composition according to the present invention can be prepared by merely mixing the ingredients.

The embodiments detailed above can be readily combined with one another non-restrictively.

The present invention will be described in more detail using the following examples which are purely illustrative.

EXAMPLES

Example 1: Perfumed Composition No. 1

The ingredients of perfumed composition No. 1, described in table 1, are mixed in order to obtain perfumed composition No. 1.

TABLE 1

| Name of product | % By weight Quantity |
|---|---|
| Perfume 1 | 20.000% |
| C12-13 Pareth-9 | 20.000% |
| Isopentyldiol | 20.000% |
| Distilled water | 39.250% |
| Phenoxyethanol, Chlorphenesin, Caprylyl Glycol | 0.750% |
| Simethicone | $1 \times 10^{-3}$% |

The ingredients of perfume 1, described in table 2, are mixed in order to obtain perfume 1.

TABLE 2

| Name of product | % By weight Quantity |
|---|---|
| Triethyl citrate | 7.000% |
| 4-tert-Butylcyclohexyl Acetate | 10.000% |
| 6-tert-Butylquinoline | 0.300% |
| (3R-(3alpha,3abeta,6beta,7beta,8aalpha))-Octahydro-6-methoxy-3,6,8,8-tetramethyl-1H-3a,7-methanoazulene | 5.000% |
| (3R-(3alpha,3abeta,6alpha,7beta,8aalpha))-Octahydro-3,6,8,8-tetramethyl-1H-3a,7-methanoazulene-5-yl Acetate | 40.000% |
| 1-(1,2,3,4,5,6,7,8-octahydro-2,3,8,8-tetramethyl-2-naphthalenyl)ethanone | 30.000% |
| Suederal LT 2010-2015 ®, IFF | 0.500% |
| 3-Methyl-4-(2,6,6-trimethyl-2-cyclohexenyl)-3-buten-2-one | 5.000% |
| 3,7-Dimethyl-2,6-octadienal | 0.500% |
| 3,7-Dimethyl octa-1,6-diene-3-yl acetate | 1.700% |

Example 2: Perfumed Composition No. 2

The ingredients of perfumed composition No. 2, described in table 3, are mixed in order to obtain perfumed composition No. 2.

TABLE 3

| Name of product | % By weight Quantity |
|---|---|
| Perfume 1 | 7.000% |
| C12-13 Pareth-9 | 8.000% |
| Isopentyldiol | 7.000% |
| Distilled water | 78.000% |

Example 3: Perfumed Composition No. 3

The ingredients of perfumed composition No. 3, described in table 4, are mixed in order to obtain perfumed composition No. 3.

TABLE 4

| Name of product | % By weight Quantity |
|---|---|
| Perfume 2 | 5.000% |
| C12-13 Pareth-9 | 9.000% |
| Isopentyldiol | 15.000% |
| Distilled water | 70.250% |
| 2-phenoxyethanol (and) Octane-1,2-diol (and) 3-(4-Chlorophenoxy)-1,2-propanediol | 0.750% |

The ingredients of perfume 2, described in table 5, are mixed in order to obtain perfume 2.

TABLE 5

| Name of product | % By weight |
|---|---|
| Isopentyl acetate | 0.017 |
| Methyl Phenylacetate | 0.500 |
| (Z)-Hex-3-enyl acetate | 0.125 |
| 3,7-Dimethyl octa-1,6-diene-3-yl acetate | 2.500 |
| 3-Methyl-2-butenyl acetate | 0.017 |
| Benzenemethanol, a-Methyl-, Acetate | 0.125 |
| Undecanal | 0.008 |
| Undecan-4-olide | 0.017 |
| Benzenepropanal, .alpha.-methyl-4-(1-methylethyl)- | 0.008 |
| (3aR-(3aalpha,5abeta,9aalpha,9bbeta))-Dodecahydro-3a,6,6,9a-tetramethylnaphtho(2,1-b)furan | 0.042 |
| Methyl 2-aminobenzoate | 0.042 |
| 2-Phenylethanol | 0.833 |
| cis-Hex-3-en-1-ol | 0.125 |
| 4-Methyl-3-decen-5-ol | 0.083 |
| 7-Methyl-2H-benzo-1,5-dioxepin-3(4H)-one | 0.042 |
| 2-Propenyl (cyclohexyloxy)acetate | 0.042 |
| Decan-5-olide | 0.008 |
| 1-(2,6,6-Trimethyl-1,3-cyclohexadienyl)-2-buten-1-one | 0.025 |
| 2,6-dimethyloct-7-en-2-ol | 0.017 |
| 1,1'-Oxydipropan-2-ol; | 52.764 |
| 3,7-Dimethyl-1,6-nonadien-3-ol | 1.667 |
| Lemon oil (Citrus Limon Fruit Oil) | 0.833 |
| Methyl hydroxypyrone | 0.001 |
| 2,2,5-Trimethyl-5-pentylcyclopentan-1-one | 0.027 |
| 3,4,4a,5,8,8a-Hexahydro-3',7'-dimethylspiro(1,4-methanonaphthalene-2(1H),2'-oxirane) | 0.002 |
| cis-2-Methyl-4-propyl-1,3-oxathiane | 0.002 |
| Methyl 2,4-dihydroxy-3,6-dimethylbenzoate | 0.033 |
| 2,4-dimethylcyclohex-3-ene-1-carbaldehyde | 0.052 |
| methyl 3-oxo-2-pentylcyclopentaneacetate | 20.018 |

TABLE 5-continued

| Name of product | % By weight |
|---|---|
| Triethyl citrate | 0.080 |
| 1-(5,5-Dimethyl-1-cyclohexenyl)pent-4-en-1-one | 0.001 |
| 3,7-Dimethyl-6-octen-1-ol | 0.005 |
| 6,6-Dimethyl-2-methylenebicyclo[3.1.1]heptane | 0.013 |
| 2,6,6-Trimethylbicyclo[3.1.1]hept-2-ene | 0.001 |
| Pogostemon Cablin Leaf Oil | 0.042 |
| Tetrahydro-4-methyl-2-(2-methylpropyl)-2H-pyran-4-ol | 5.417 |
| 1,4-Dioxacycloheptadecane-5,17-dione | 6.250 |
| Decan-4-olide | 0.042 |
| alpha-Methyl-1,3-benzodioxole-5-propionaldehyde | 1.250 |
| (E)-4-(2,6,6-trimethyl-1-cyclohexen-1-yl)-3-buten-2-one | 1.667 |
| 2-ethoxy-4-(methoxymethyl)-Phenol | 0.017 |
| 3,7-Dimethyl octa-1,6-diene-3-ol | 2.083 |
| 1,4-Dioxacyclohexadecane-5,16-Dione | 0.017 |
| 3-Methyl-5-cyclopentadecen-1-one | 0.083 |
| benzyl 2-hydroxybenzoate | 0.583 |
| (Z)-3-Hexenyl 2-hydroxybenzoate | 0.583 |
| p-menth-1-en-8-ol | 0.008 |
| 2-(1,1-Dimethylethyl) Cyclohexyl Acetate | 0.025 |
| Citrus nobilis peel oil | 0.833 |
| Citrus Aurantium Dulcis (Orange) Peel Oil | 0.833 |
| 2,4,6-Trimethyl-4-phenyl-1,3-dioxane | 0.025 |
| 4-(2,6,6-Trimethylcyclohex-2-eneyl)-but-3-ene-2-one | 0.167 |

Example 4: Perfumed Composition No. 4

The ingredients of perfumed composition No. 4, described in table 6, are mixed in order to obtain perfumed composition No. 4.

TABLE 6

| Name of product | % By weight Quantity |
|---|---|
| Perfume 3 | 12.000% |
| C12-13 Pareth-9 | 13.000% |
| Isopentyldiol | 15.000% |
| Distilled water | 59.250% |
| 2-phenoxyethanol (and) Octane-1,2-diol (and) 3-(4-Chlorophenoxy)-1,2-propanediol | 0.750% |

The ingredients of perfume 3, described in table 7, are mixed in order to obtain perfume 3.

TABLE 7

| Name of product | % By weight |
|---|---|
| 1,1'-Oxydipropan-2-ol | 30.47% |
| 2,6-dimethyloct-7-en-2-ol | 10.77% |
| 3,7-Dimethyl octa-1,6-diene-3-ol | 9.23% |
| methyl 3-oxo-2-pentylcyclopentaneacetate | 6.15% |
| 2-(1,1-Dimethylethyl) Cyclohexyl Acetate | 4.62% |
| 2-Phenylethanol | 3.85% |
| 2-ethyl-4-(2,2,3-trimethyl-3-cyclopenten-1-yl)-2-buten-1-ol | 3.08% |
| Benzoic acid, 2-hydroxy-, 2-hexyl ester | 3.08% |
| 3a,4,5,6,7,7a-Hexahydro-4,7-methanoinden-6-yl Acetate | 3.08% |
| phenylmethanol | 2.31% |
| 4-Methyl-3-decen-5-ol | 2.15% |
| 3-Methyl-4-(2,6,6-trimethyl-2-cyclohexenyl)-3-buten-2-one | 1.69% |
| 2-[2-(4-Methyl-3-cyclohexen-1-yl)propyl]-cyclopentanone | 1.54% |
| 3a,4,5,6,7,7a-Hexahydro-4,7-methano-1H-inden-6-yl Propanoate | 1.54% |
| Citrus Aurantium Dulcis Flower Extract | 1.54% |
| 1-(1,2,3,4,5,6,7,8-octahydro-2,3,8,8-tetramethyl-2-naphthalenyl)ethanone | 1.54% |
| 2,6-Dimethyloctan-2-ol | 1.23% |
| Benzene, 1,1'-Oxybis | 1.08% |

TABLE 7-continued

| Name of product | % By weight |
|---|---|
| 2-Isopropyl-4-methyl-1,3-thiazole | 0.01% |
| Triethyl citrate | 1.07% |
| 3,7-Dimethyl-6-octen-1-ol | 1.08% |
| 2,4-dimethylcyclohex-3-ene-1-carbaldehyde | 0.92% |
| (E)-4-(2,6,6-trimethyl-1-cyclohexen-1-yl)-3-buten-2-one | 0.77% |
| Methyl 2-naphthyl ether | 0.77% |
| Undecan-4-olide | 0.62% |
| 4-Phenylbutan-2-one | 0.62% |
| 2-Cyclohexyl-1,6-heptadien-3-one | 0.46% |
| Cyclohexanol, 4-(1,1-dimethylethyl)- | 0.46% |
| ethyl 2-methylbutyrate | 0.46% |
| 3a,4,5,6,7,7a-Hexahydro-4,7-methano-1H-inden-5-yl 2-methylpropanoate | 0.46% |
| 2-Methyl-1-phenylpropan-2-ol | 0.46% |
| alpha, alpha-Dimethylphenethyl Acetate | 0.46% |
| 2,6-Octadien-1-ol, 3,7-dimethyl-, (2E)- | 0.31% |
| 3,7-Dimethyl octa-1,6-diene-3-yl acetate | 0.31% |
| Hexan-1-ol | 0.15% |
| Bicyclo[2.2.1]heptan-2-ol, 1,7,7-trimethyl-, acetate, exo- | 0.15% |
| Decan-4-olide | 0.15% |
| 1-(5,5-Dimethyl-1-cyclohexenyl)pent-4-en-1-one | 0.15% |
| exo-1,7,7-Trimethylbicyclo[2.2.1]heptan-2-ol | 0.15% |
| 2-Buten-1-one, 1-(2,6,6-trimethyl-3-cyclohexen-1-yl)- | 0.15% |
| ethyl hexanoate | 0.15% |
| 2H-1-Benzopyran-2-one | 0.15% |
| 2-(2,2,7,7-tetramethyltricyclo[6.2.1.0 (1,6)]undec-5(4)-en-5-yl)propan-1-ol | 0.15% |
| 3,7-Dimethyloct-6-enenitrile | 0.15% |
| Benzaldehyde | 0.09% |
| 1-spiro(4.5)-7-decen-7-yl-4-penten-1-one and 1-spiro(4.5)-6-decen-7-yl-4-penten-1-one | 0.08% |
| 1-Phenylethanol | 0.08% |
| ethyl 2-naphthyl ether | 0.06% |

Example 5: Perfumed Composition No. 5

The ingredients of perfumed composition No. 5, described in table 8, are mixed in order to obtain perfumed composition No. 5.

TABLE 8

| Name of product | % By weight Quantity |
|---|---|
| Perfume 4 | 15.000% |
| C12-13 Pareth-9 | 15.000% |
| Isopentyldiol | 15.000% |
| Distilled water | 54.250% |
| 2-phenoxyethanol (and) Octane-1,2-diol (and) 3-(4-Chlorophenoxy)-1,2-propanediol | 0.750% |

The ingredients of perfume 4, described in table 9, are mixed in order to obtain perfume 4.

TABLE 9

| Name of product | % By weight |
|---|---|
| 1,1'-Oxydipropan-2-ol | 60.620% |
| 3,7-Dimethyloctan-3-ol | 6.897% |
| 3,7-Dimethyl octa-1,6-dien-3-yl acetate | 5.172% |
| 3,7-Dimethyloct-6-enenitrile | 2.069% |
| cis-3,7-Dimethyl-2,6-octadien-1-ol | 2.414% |
| methyl 3-oxo-2-pentylcyclopentaneacetate | 3.793% |
| (2E)-2-Dodecenal | 0.161% |
| 3,7-Dimethyl-6-octen-1-ol | 3.448% |
| (E)1-(2,6,6-Trimethyl-2-cyclohexen-1-yl)-2-buten-1-one | 0.276% |

TABLE 9-continued

| Name of product | % By weight |
|---|---|
| (E)-4-(2,6,6-trimethyl-1-cyclohexen-1-yl)-3-buten-2-one | 2.207% |
| Decanal | 2.414% |
| cis-Hex-3-en-1-ol; | 0.621% |
| 3,7-Dimethyl-2,6-octadienal | 2.069% |
| Methyl 2-(methylamino)benzoate | 0.483% |
| Hex-2-en-1-ol | 0.138% |
| GALBEX 183 EB ®, Firmenich | 0.011% |
| Undeca-1,3,5-triene | 0.002% |
| Phenol, 5-methyl-2-(1-methylethyl)- | 0.065% |
| 1-Methyl-4-(1-methylethyl)benzene | 0.214% |
| cis-2-Methyl-4-propyl-1,3-oxathiane | 0.035% |
| 3,7-Dimethyl octa-1,6-diene-3-ol | 0.081% |
| Octanal | 0.139% |
| Lauryl aldehyde | 0.001% |
| 2-Methyl-4-phenylbutan-2-ol | 0.621% |
| Nonanal | 0.345% |
| Citrus Aurantium Dulcis (Orange) Peel Oil | 0.552% |
| Dihydro-5-pentyl-2(3H)-furanone | 0.069% |
| 2,4-Dimethyl-4-phenyltetrahydrofuran | 0.024% |
| 10-Undecenoic Acid, ethyl Ester | 0.024% |
| ethyl 2-methylpentanoate | 0.021% |
| 2,6-Octadien-1-ol, 3,7-dimethyl-, (2E)- | 0.276% |
| cis-3,7-Dimethyl-2,6-octadienyl ethanoate | 0.552% |
| 2,2,5-Trimethyl-5-pentylcyclopentan-1-one | 0.276% |
| p-menth-1-en-8-ol | 0.041% |
| 1-(1,2,3,4,5,6,7,8-octahydro-2,3,8,8-tetramethyl-2-naphthalenyl)ethanone | 1.034% |
| (E)-2-Benzylideneoctanal | 0.552% |
| 2,4-dimethylcyclohex-3-ene-1-carbaldehyde | 0.552% |
| 1,4-Dioxacycloheptadecane-5,17-dione | 0.414% |
| Barosma Betulina Leaf Extract | 0.345% |
| Bicyclo[7.2.0.]undec-4-ene, 4,11,11-trimethyl-8-methylene-, (1R,4E,9S) | 0.014% |
| 3-(4-ethylphenyl)-2,2-dimethylpropanal | 0.276% |
| benzyl 2-hydroxybenzoate | 0.069% |
| (Z)-Hex-3-enyl acetate | 0.345% |
| 2,6-dimethyloct-7-en-2-ol | 0.041% |
| 4-Hydroxy-3-methoxybenzaldehyde | 0.069% |
| 2H-1-Benzopyran-2-one | 0.034% |
| Decan-4-olide | 0.041% |
| Benzoic acid, 2-hydroxy-, 2-hexyl ester | 0.028% |
| 2-Propenyl (cyclohexyloxy)acetate | 0.048% |
| Acetic acid, (3-Methylbutoxy), 2-Propenyl Ester | 0.007% |

Example 6: Perfumed Composition No. 6

The ingredients of perfumed composition No. 6, described in table 10, are mixed in order to obtain perfumed composition No. 6.

TABLE 10

| Name of product | % By weight Quantity |
|---|---|
| Perfume 5 | 40.000% |
| C12-13 Pareth-9 | 25.000% |
| Isopentyldiol | 15.000% |
| Distilled water | 19.250% |
| 2-phenoxyethanol (and) Octane-1,2-diol (and) 3-(4-Chlorophenoxy)-1,2-propanediol | 0.750% |

The ingredients of perfume 5, described in table 11, are mixed in order to obtain perfume 5.

TABLE 11

| Name of product | % By weight |
|---|---|
| 2-Phenylethanol | 40.00% |
| Phenethyl acetate | 10.00% |
| 3-Phenylpropan-1-ol | 15.00% |
| Hexyl acetate | 5.00% |
| (1R, 2S, 5R)-5-Methyl-2-(1-methylethyl)-cyclohexanol ethanoate phenylmethanol | 10.00% 20.00% |

Example 7: Perfume Complex No. 1

The ingredients described in table 12, are mixed in order to obtain perfume complex No. 1.

TABLE 12

| Name of product | % By weight Quantity |
|---|---|
| Perfume 2 | 28.000% |
| C12-13 Pareth-9 | 26.000% |
| Isopentyldiol | 46.000% |

Example 8: Perfume Composition No. 7

The ingredients described in table 13, are mixed in order to obtain perfume composition No. 7.

TABLE 13

| Name of product | % By weight Quantity |
|---|---|
| Perfume complex No. 1 | 35.000% |
| Distilled water | 64.250% |
| 2-phenoxyethanol (and) Octane-1,2-diol (and 3-(4-Chlorophenoxy)-1,2-propanediol | 0.750% |

Example 9: Perfume Complex No. 2

The ingredients described in table 14, are mixed in order to obtain perfume complex No. 2.

TABLE 14

| Name of product | % By weight Quantity |
|---|---|
| Perfume 2 | 23.300% |
| C12-13 Pareth-9 | 26.700% |
| Isopentyldiol | 50.000% |

Example 10: Perfume Composition No. 8

The ingredients described in table 15, are mixed in order to obtain perfume composition No. 8.

TABLE 15

| Name of product | % By weight Quantity |
| --- | --- |
| Perfume complex No. 2 | 35.000% |
| Distilled water | 64.250% |
| 2-phenoxyethanol (and) Octane-1,2-diol (and 3-(4-Chlorophenoxy)-1,2-propanediol | 0.750% |

Perfumed compositions No. 7 and No. 8 are transparent, low-tack and have a strong smell.

Comparative Example 1: Comparative Perfumed Composition A

The ingredients of comparative perfumed composition A, described in table 16, are mixed in order to obtain comparative perfumed composition A.

TABLE 16

| Name of product | % By weight Quantity |
| --- | --- |
| Mixture consisting of citronellol, dihydro myrcenol, ethyl linalol, and linalool | 7.000% |
| Surfactant mixture A | 8.000% |
| Isopentyldiol | 7.000% |
| Isosorbide dimetylether | 6.000% |
| Distilled water | 72.000% |

Surfactant mixture A is prepared by mixing 40-60 wt. % trideceth-9, 20-40 wt. % PEG 40 hydrogenated castor oil and up to 5 wt. % Polysorbate-20.

Comparative Example 2: Comparative Perfumed Composition B

The ingredients of comparative perfumed composition B, described in table 17, are mixed in order to obtain comparative perfumed composition B.

TABLE 17

| Name of product | % By weight Quantity |
| --- | --- |
| Perfume 1 | 20.000% |
| Hexanediol | 20.000% |
| Distilled water | 59.250% |
| Phenoxyethanol, Chlorphenesin, Caprylyl Glycol | 0.750% |
| Simethicone | $1 \times 10^{-3}$% |

Comparative Example 3: Comparative Perfumed Composition C

The ingredients of comparative perfumed composition C, described in table 18, are mixed in order to obtain comparative perfumed composition C.

TABLE 18

| Name of product | % By weight Quantity |
| --- | --- |
| Isopentyl acetate | 0.002% |
| Methyl Phenylacetate | 0.060% |
| (Z)-Hex-3-enyl acetate | 0.015% |
| 3,7-Dimethyl octa-1,6-diene-3-yl acetate | 0.300% |
| 3-Methyl-2-butenyl acetate | 0.002% |
| Benzenemethanol, a-Methyl-, Acetate | 0.015% |
| Undecanal | 0.001% |
| Undecan-4-olide | 0.002% |
| Benzenepropanal, .alpha.- methyl-4-(1-methylethyl)- | 0.001% |
| (3aR-(3aalpha,5abeta,9aalpha,9bbeta))-Dodecahydro-3a,6,6,9a-tetramethylnaphtho(2,1-b)furan | 0.005% |
| Methyl 2-aminobenzoate | 0.005% |
| 2-Phenylethanol | 0.100% |
| cis-Hex-3-en-1-ol | 0.015% |
| 4-Methyl-3-decen-5-ol | 0.010% |
| 7-Methyl-2H-benzo-1,5-dioxepin-3(4H)-one | 0.005% |
| 2-Propenyl (cyclohexyloxy)acetate | 0.005% |
| Decan-5-olide | 0.001% |
| 1-(2,6,6-Trimethyl-1,3-cyclohexadienyl)-2-buten-1-one | 0.003% |
| 2,6-dimethyloct-7-en-2-ol | 0.002% |
| 1,1'-Oxydipropan-2-ol | 6.327% |
| 3,7-Dimethyl-1,6-nonadien-3-ol | 0.200% |
| Lemon oil (Citrus Limon Fruit Oil) | 0.100% |
| Methyl hydroxypyrone | 0.001% |
| 2,2,5-Trimethyl-5-pentylcyclopentan-1-one | 0.003% |
| 3,4,4a,5,8,8a-Hexahydro-3',7'-dimethylspiro(1,4-methanonaphthalene-2(1H),2'-oxirane) | 0.001% |
| cis-2-Methyl-4-propyl-1,3-oxathiane | 0.001% |
| Methyl 2,4-dihydroxy-3,6-dimethylbenzoate | 0.004% |
| 2,4-dimethylcyclohex-3-ene-1-carbaldehyde | 0.006% |
| methyl 3-oxo-2-pentylcyclopentaneacetate | 2.402% |
| Triethyl citrate | 0.010% |
| 1-(5,5-Dimethyl-1-cyclohexenyl)pent-4-en-1-one | 0.001% |
| 3,7-Dimethyl-6-octen-1-ol | 0.001% |
| 6,6-Dimethyl-2-methylenebicyclo[3.1.1]heptane | 0.002% |
| 2,6,6-Trimethylbicyclo[3.1.1]hept-2-ene | 0.001% |
| Pogostemon Cablin Leaf Oil | 0.005% |
| Tetrahydro-4-methyl-2-(2-methylpropyl)-2H-pyran-4-ol | 0.650% |
| 1,4-Dioxacycloheptadecane-5,17-dione | 0.750% |
| Decan-4-olide | 0.005% |
| alpha-Methyl-1,3-benzodioxole-5-propionaldehyde | 0.150% |
| (E)-4-(2,6,6-trimethyl-1-cyclohexen-1-yl)-3-buten-2-one | 0.200% |
| 2-ethoxy-4-(methoxymethyl)-Phenol | 0.002% |
| 3,7-Dimethyl octa-1,6-dien-3-ol | 0.250% |
| 1,4-Dioxacyclohexadecane-5,16-Dione | 0.002% |
| 3-Methyl-5-cyclopentadecen-1-one | 0.010% |
| Benzyl salicylate | 0.070% |
| (Z)-3-Hexenyl 2-hydroxybenzoate | 0.070% |
| p-menth-1-en-8-ol | 0.001% |
| 2-(1, 1-Dimethylethyl) Cyclohexyl Acetate | 0.003% |
| Citrus nobilis peel oil | 0.100% |
| Citrus Aurantium Dulcis (Orange) Peel Oil | 0.100% |
| 2,4,6-Trimethyl-4-phenyl-1,3-dioxane | 0.003% |
| 4-(2,6,6-Trimethylcyclohex-2-eneyl)-but-3-ene-2-one | 0.020% |
| C12-13 Pareth-9 | 4.000% |
| Isopentyldiol | 15.000% |
| Water | 68.250% |
| 2-phenoxyethanol (and) Octane-1,2-diol (and) 3-(4-Chlorophenoxy)-1,2-propanediol | 0.750% |

Comparative Example 4: Comparative Perfumed Composition D

The ingredients of comparative perfumed composition D, described in table 19, are mixed in order to obtain comparative perfumed composition D.

TABLE 19

| Name of product | % By weight Quantity |
|---|---|
| Methyl Phenylacetate | 0.053% |
| 3,7-Dimethyl octa-1,6-diene-3-yl acetate | 0.255% |
| phenylmethanol | 0.135% |
| Undecan-4-olide | 0.023% |
| Artemisia herba-alba herb oil | 0.004% |
| cis-Hex-3-en-1-ol | 0.002% |
| Citrus limon (lemon) peel oil | 0.975% |
| Citrus limon peel extract | 0.492% |
| 6-Octenal, 3,7-dimethyl- | 0.002% |
| 3,7-Dimethyl-6-octen-1-ol | 0.292% |
| 1,1'-Oxydipropan-2-ol | 0.915% |
| Geranyl acetate | 0.006% |
| cis-3,7-Dimethyl-2,6-octadienyl ethanoate | 0.008% |
| 2,6,6-Trimethylbicyclo[3.1.1]hept-2-ene | 0.011% |
| 6,6-Dimethyl-2-methylenebicyclo[3.1.1]heptane | 0.407% |
| 2,6-Octadien-1-ol, 3,7-dimethyl-, (2E)- | 0.000% |
| cis-3,7-Dimethyl-2,6-octadien-1-ol | 0.026% |
| 3,7-Dimethyl-1-octanol; | 0.001% |
| 1-Methyl-4-isopropenyl-1-cyclohexene | 0.009% |
| 2,6-Octadienal, 3,7-dimethyl- | 1.053% |
| 3,7-Dimethyl octa-1,6-diene-3-ol | 0.151% |
| p-menth-1-en-8-ol | 0.009% |
| 4-Methyl-1-(1-methylethyl)-3-cyclohexen-1-ol | 0.002% |
| 1-Methyl-4-isopropyl-1,3-cyclohexadiene; | 0.072% |
| Citrus aurantium dulcis peel extract | 3.916% |
| Eucalyptus globulus Leaf Extract | 0.001% |
| p-Menth-1-en-8-ol | 0.004% |
| 2,6-Octadien-1-ol, 3,7-dimethyl-, (2E)- | 1.351% |
| 2-(Tetrahydro-5-methyl-5-vinyl-2-furyl) propan-2-ol | 0.002% |
| Litsea cubeba fruit oil | 1.688% |
| Myrocarpus Fastigiatus Oil | 0.001% |
| Coriandrum sativum fruit oil | 0.001% |
| Pelargonium graveolens flower oil | 0.375% |
| methyl 3-oxo-2-pentylcyclopentaneacetate | 1.875% |
| Indole | 0.012% |
| 2-Phenylmethyleneoctanal | 0.690% |
| cis-Hex-3-enyl methyl carbonate | 0.006% |
| Citrus nobilis peel oil | 0.018% |
| 6-Methylhept-5-en-2-one | 0.001% |
| 1-Methyl-4-(1-methylethyl)benzene | 0.120% |
| Citrus aurantium amara leaf oil | 0.026% |
| Citrus limonum leaf oil | 0.012% |
| C12-13 Pareth-9 | 15.000% |
| Isopentyldiol | 4.000% |
| Water | 65.250% |
| 2-phenoxyethanol (and) Octane-1,2-diol (and) 3-(4-Chlorophenoxy)-1,2-propanediol | 0.750% |

Profile Challenge

Test Preparation

The purpose of the test is to reveal the similarities and differences between products in the form, particularly of "sensory charts" with 32 panellists.

During this test, 3 perfume descriptors were evaluated: "glide", "absorption", and "perfume intensity".

For each descriptor, a precise protocol was given to the panellists so that all the panellists evaluate the descriptors identically.

The panellists were also requested to wash their hands between each reference tested with hydroalcoholic gel in order to prevent any cross-contamination.

The references evaluated were encoded in order to evaluate the products blind.

"Glide" denotes the evaluation of the physical property of frictional resistance of the product.

For this test, a drop of the composition to be studied is placed on the panellist's forefinger and a rubbing movement between the panellist's forefinger and thumb is performed. The rubbing is then evaluated. The result is reported on a scale ranging from 3 (very good), i.e. the movement is easy, there is no resistance to 0 (unacceptable), i.e. the movement is difficult, there is a strong resistance.

"Absorption" denotes the evaluation of the physical property of product penetration.

For this test, a drop of the composition to be studied is placed on the inside of the panellist's forearm, and the drop is spread by performing 15 manual movements (15 glides). The penetration is then evaluated. The result is reported on a scale ranging from 3 (very good), i.e. the penetration is good and there is no product residue, to 0 (unacceptable), i.e. the penetration is poor and there is a product residue.

"Perfume intensity" denotes the evaluation of the olfactory property of the product after application.

After the spreading of the product performed previously, the panellists placed their noses a few centimetres from their skin, and the rating of the olfactory intensity of the perfume is evaluated. The results is reported on a scale ranging from 3 (very good), i.e. good perception and intense perfume, to 0 (unacceptable), i.e. poor perception and overly weak perfume.

Only 2 references are evaluated per test, one on the left arm applying the product with the right hand and the second product on the right arm applying the product with the left hand.

Results

Figure 1:
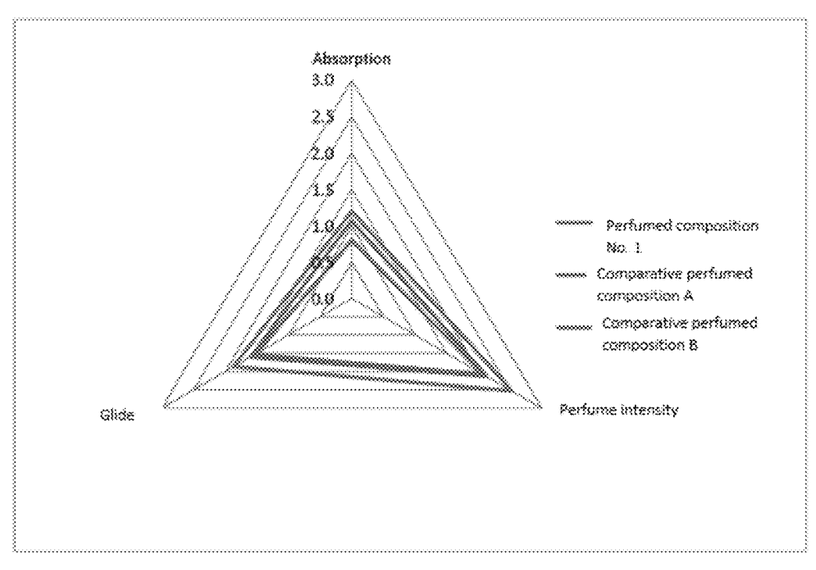
FIG. 1 shows the results of sensory charts test, ranging from 0 to 3 in intervals of 0.5, as described in the description.

The results, ranging from 0 to 3 in intervals of 0.5, are shown in FIG. 1.

The composition according to the present invention (perfumed composition No. 1) has a superior penetration, perfume intensity and frictional resistance to comparative compositions A and B studied.

Thus, the composition according to the present invention is significantly superior to the comparative perfumed compositions for the absorption, glide, and perfume intensity descriptors.

Additional Tests

After having compared the transparency of perfumed composition No. 1 with that of comparative composition B, the present inventors demonstrated that the use of vicinal diol (see comparative composition B) renders the solution opaque. On the other hand, perfumed composition No. 1 according to the invention, free from vicinal diol, is transparent.

After having compared the transparency of perfumed compositions No. 1 to 6 with that of comparative composition C, the present inventors demonstrated that the use of C12-13 pareth-9 at a quantity less than 5 wt. % with respect to the total weight of the perfumed composition renders the perfumed composition opaque.

After having compared the transparency of perfumed compositions No. 1 to 6 with that of comparative composition D, the present inventors demonstrated that the use of isopentyldiol at a quantity less than 5 wt. % with respect to the total weight of the perfumed composition renders the composition opaque. In particular, using isopentyldiol at a quantity less than 5 wt. % with respect to the total weight of the perfumed composition, the perfumed composition clouds and becomes opaque.

It was also demonstrated that the perfumed compositions according to the present invention (see perfumed compositions No. 1 to 6) are transparent under temperature conditions ranging from 4 to 50° C., regardless of the perfume used (including a perfume containing less than 18 wt. % branched alcohol with at least 8 carbon atoms), at dosages ranging from 5 to 40%.

After studying the perfume intensity of perfumed compositions No. 1 to 6, it was demonstrated that a composition according to the invention had a greater olfactory degree than that of comparative compositions A, B, C and D.

Perfumed compositions No. 1 to 6 are low-tack and low-foam, do not evaporate too quickly and have enhanced solubility and olfactory performance compared with comparative compositions A, B, C and D.

Comparative Example 5: Comparison of C12-13 Pareth-9 Versus Barsolve Plus

The efficacy of C12-13 Pareth-9 was tested against that of Barsolve Plus, a mixture of 40-60% Trideceth-9, 20-40% PEG-40 Hydrogenated Castor oil, 5% Polysorbate-20, marketed by Barnet (Table 20).

The ingredients of phase (A) are all added at ambient temperature into a beaker under stirring. After homogenisation, the perfume (B) is added under constant gentle stirring. The perfume tested herein, in phase (B), is composed of 32 wt. % branched alcohols with at least 8 carbon atoms (mixture of citronellol, dihydromyrcenol, ethyl linalool and linalool).

TABLE 20

| Raw materials | Test 1 | Test 2 |
| --- | --- | --- |
| Perfume (B) | 7.00 | 7.00 |
| Isopentyldiol (A) | 7.00 | 7.00 |
| C12-13 Pareth-9 (A) | 8.00 | — |
| Barsolve Plus (A) | — | 8.00 |
| Deionised water (A) | 78.00 | 78.00 |
| Result at ambient temperature | C | D |

Comparative Tests of the Efficacy of C12-13 Pareth-9 Versus Barsolve Plus (Cited in WO2014/187950)

Key:
C=clear, transparent
V=veiled, blue
T=turbid, cloudy
D=dephased

In the light of the results above, after comparing test 1 with test 2, at the same perfume, isopentyldiol and solubilising agent dosage, we observe that C12-13 Pareth-9 makes it possible to obtain a clear solution at ambient temperature unlike Barsolve Plus when it is used without a co-solvent. The solubilising agent C12-13 Pareth-9 therefore has a superior solubilising power to Barsolve Plus. It is therefore concluded that, unlike C12-13 Pareth-9, Barsolve Plus is not effective without a co-solvent. C12-13 Pareth-9 is effective without an additional co-solvent.

Tests were then carried out at higher perfume, isopentyldiol and solubilising agent dosages (Table 21). The addition of a co-solvent, Isosorbide dimethylether, to Barsolve Plus was also tested.

As the solutions obtained are all clear, stability tests are performed under the following conditions: 3 days in a refrigerator at 5° C., 3 days in a thermostatically controlled cabinet (respectively at 40° C., 45° C. and 50° C.) and 24 h in UV (test carried out with a Labomat Q-SUN Xe-1-B apparatus, Xenon lamp, at a wavelength of 420 nm, with an irradiance of 0.62 W/m$^2$).

TABLE 21

| Raw materials | Test 3 | Test 4 | Test 5 |
| --- | --- | --- | --- |
| Perfume (B) | 10.00 | 10.00 | 10.00 |
| Isopentyldiol (A) | 16.00 | 16.00 | 16.00 |
| C12-13 Pareth-9 (A) | 9.00 | — | — |
| Barsolve Plus (A) | — | 9.00 | 9.00 |
| Isosorbide dimethylether (A) | — | — | 6.00 |
| Deionised water (A) | 65.00 | 65.00 | 59.00 |
| Stability tests | Test 3 | Test 4 | Test 5 |
| 5° C. | C | D | D |
| AT | C | C | C |
| 40° C. | C | C | C |
| 45° C. | C | C | C |
| 50° C. | C | C | C |
| UV | C | V | C |

Comparative Tests of C12-13 Pareth-9 Versus Barsolve Plus at High Dosages

In the light of the results above, after comparing test 3 with test 4, we observe that C12-13 Pareth-9 makes it possible to obtain a superior stability at 5° C. and in UV. It is therefore concluded that, unlike C12-13 Pareth-9, Barsolve Plus does not make it possible to obtain a stable solution at 5° C., or in UV when it is used without a co-solvent, when the perfume dosage is 10%. C12-13 Pareth-9 makes it possible to obtain a stable solution with 10% perfume, under all test conditions, without an additional co-solvent.

In the light of the results above, after comparing test 3 with test 5, we observe that C12-13 Pareth-9 makes it possible to obtain a superior stability at 5° C. It is therefore concluded that, unlike C12-13 Pareth-9, Barsolve Plus does not make it possible to obtain a stable solution at 5° C. even when it is used with a co-solvent, when the perfume dosage is 10%. C12-13 Pareth-9 makes it possible to obtain a stable solution with 10% perfume under all test conditions, without an additional co-solvent.

Comparative Example 6: Comparison of the Quantities of Isopentyldiol Required to Obtain Clear Solutions at Ambient Temperature Tests were carried out at the same perfume and solubilising agent dosage, in order to determine the quantity of isopentyldiol required to obtain clear solutions at ambient temperature (Table 22).

TABLE 22

| Raw materials | Test 3 | Test 6 | Test 7 | Test 4 | Test 8 | Test 9 | Test 5 | Test 10 | Test 11 |
| --- | --- | --- | --- | --- | --- | --- | --- | --- | --- |
| Perfume (B) | 10.00 | 10.00 | 10.00 | 10.00 | 10.00 | 10.00 | 10.00 | 10.00 | 10.00 |
| Isopentyldiol (A) | 16.00 | 12.00 | 10.00 | 16.00 | 12.00 | 10.00 | 16.00 | 12.00 | 10.00 |
| C12-13 Pareth-9 (A) | 9.00 | 9.00 | 9.00 | — | — | — | — | — | — |

TABLE 22-continued

| Raw materials | Test 3 | Test 6 | Test 7 | Test 4 | Test 8 | Test 9 | Test 5 | Test 10 | Test 11 |
|---|---|---|---|---|---|---|---|---|---|
| Barsolve Plus | — | — | — | 9.00 | 9.00 | 9.00 | 9.00 | 9.00 | 9.00 |
| Isosorbide dimethylether (A) | — | — | — | — | — | — | 6.00 | 6.00 | 6.00 |
| Deionised water (A) | 65.00 | 69.00 | 71.00 | 65.00 | 69.00 | 71.00 | 59.00 | 63.00 | 65.00 |
| Result at ambient temperature | C | C | C | C | D | T | C | C | T |

Comparative Tests of Quantities of Isopentyldiol Required

In the light of the results above, after comparing tests 3, 6 and 7, C12-13 Pareth-9 makes it possible to obtain clear solutions at ambient temperature with quantities of isopentyldiol of 16%, 12% and even 10%.

In the light of the results above, after comparing tests 4, 8 and 9, Barsolve Plus, used without a co-solvent, makes it possible to obtain clear solutions at ambient temperature with a quantity of isopentyldiol of 16%. It is therefore concluded that, Barsolve Plus used without a co-solvent, requires a greater quantity of isopentyldiol than C12-13 Pareth-9 to obtain clear solutions at ambient temperature.

In the light of the results above, after comparing tests 5, 10 and 11, Barsolve Plus, used with a co-solvent, makes it possible to obtain clear solutions at ambient temperature with quantities of isopentyldiol of 16% and 12%. It is therefore concluded that, Barsolve Plus used with a co-solvent, requires a greater quantity of isopentyldiol than C12-13 Pareth-9 to obtain clear solutions at ambient temperature.

C12-13 Pareth-9 therefore requires less isopentyldiol and does not require any other co-solvent to obtain clear and stable solutions.

The invention claimed is:

1. A perfume complex not comprising water and comprising three basic ingredients as follows: from 15 to 45 wt. % of perfume, from 15 to 50 wt. % of isopentyldiol and from 15 to 30 wt. % of C12-13 pareth-9, the percentages being expressed with respect to the total weight of the three basic ingredients.

2. The perfume complex according to claim 1 being free from ethanol.

3. The perfume complex according to claim 1 consisting of the three basic ingredients.

4. The perfume complex according to claim 1 comprising from 20 to 40 wt. % of perfume.

5. The perfume complex according to claim 1 comprising from 27 to 31 wt. % of perfume.

6. The perfume complex according to claim 1 comprising from 20 to 30 wt. % of C12-13 pareth-9.

7. The perfume complex according to claim 1 comprising from 24 and 29 wt. % of C12-13 pareth-9.

8. The perfume complex according to claim 1 comprising from 35 to 50 wt. % of isopentyldiol.

9. The perfume complex according to claim 1 comprising from 42 to 47 wt. % of isopentyldiol.

10. A composition comprising the perfume complex according to claim 1 and water.

11. The composition according to claim 10 with a perfumed composition in microemulsion form.

12. The composition according to claim 10, being free from ethanol.

13. The composition according to claim 10 not containing any co-solvent from the group comprising isosorbide, solketal and ethers thereof.

14. The composition according to claim 10 comprising from 30 to 40 wt. % of perfume complex with respect to the total weight of the composition.

15. The composition according to claim 10 comprising from 5 to 40 wt. % of perfume, from 5 to 30 wt. % of C12-13 pareth-9, and from 5 to 30 wt. % of isopentyldiol, the percentages being expressed with respect to the total weight of said composition.

16. The composition according to claim 10, further comprising at least one additive chosen among anti-foaming agents, antioxidant agents, chelating agents, UV filters, preservatives, thickening agents, cosmetic active ingredients, hydrating agents, humectants, demulcents, pigments, colorants, cooling agent, pH-adjusting agents, bactericidal agents, bacteriostatic agents, insecticides, repellents and mixtures thereof.

17. The composition according to claim 10, wherein additives are from 0 to 5 wt. % with respect to the total weight of said composition.

18. The composition according to claim 10, comprising from 5.00% to 40.00 wt. % of perfume, from 5.00% to 30.00 wt. % of C12-13 pareth-9, and from 5.00% to 30.00 wt. % of isopentyldiol, the percentages being expressed with respect to the total weight of said composition.

19. The composition according to claim 10 comprising from 6.00% to 30.00 wt. % of perfume, from 7.00 to 20.00 wt. % of C12-13 pareth-9, and from 6.00% to 20.00 wt. % of isopentyldiol, the percentages being expressed with respect to the total weight of said composition.

20. The composition according to claim 10 comprising from 10.00% to 30.00 wt. % of perfume, from 10.00% to 25.00 wt. % of C12-13 pareth-9, and from 10.00% to 250.00 wt. % of isopentyldiol, the percentages being expressed with respect to the total weight of said composition.

21. The composition according to claim 10 comprising from 10.00% to 30.00 wt. % of perfume, from 10.00 to 20.00 wt. % of C12-13 pareth-9, and from 10.00% to 20.00 wt. % of isopentyldiol, the percentages being expressed with respect to the total weight of said composition.

22. The composition according to claim 10 comprising from 5.00% to 40.00 wt. % of perfume, from 10.00 to 20.00 wt. % of C12-13 pareth-9, and from 5.00% to 30.00 wt. % of isopentyldiol, the percentages being expressed with respect to the total weight of said composition.

23. The composition according to claim 10, comprising from 10.00% to 40.00 wt. % of perfume, from 15.00 to 25.00 wt. % of C12-13 pareth-9, and from 10.00% to 20.00 wt. % of isopentyldiol, the percentages being expressed with respect to the total weight of said composition.

24. A cosmetic base, a detergent base or an ambience perfume comprising the composition as defined according to claim 10.

\* \* \* \* \*